United States Patent
Bartels

(10) Patent No.: US 6,718,571 B2
(45) Date of Patent: Apr. 13, 2004

(54) PATIENT GURNEY AND PATIENT SUPPORT MECHANISM

(75) Inventor: Frank Bartels, Weidenberg (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 10/126,011

(22) Filed: Apr. 19, 2002

(65) Prior Publication Data

US 2002/0174485 A1 Nov. 28, 2002

(30) Foreign Application Priority Data

Apr. 20, 2001 (DE) .......................................... 101 19 453

(51) Int. Cl.[7] .............................................. A61G 7/08
(52) U.S. Cl. ..................... 5/81.1 R; 5/81.1 HS; 5/86.1; 5/601
(58) Field of Search ................... 5/81.1 HS, 601, 5/81.1 R, 86.1, 611; 108/49, 143; 248/188.1

(56) References Cited

U.S. PATENT DOCUMENTS

| | | | | |
|---|---|---|---|---|
| 2,565,761 A | * | 8/1951 | Dean ............................. | 5/86.1 |
| 2,691,782 A | * | 10/1954 | West ....................... | 5/81.1 HS |
| 2,937,765 A | * | 5/1960 | Shank ......................... | 108/143 |
| 3,339,503 A | * | 9/1967 | Flodell ........................ | 108/158 |
| 3,504,386 A | * | 4/1970 | Rossi ............................ | 5/87.1 |
| 3,606,112 A | * | 9/1971 | Cheshier ...................... | 224/554 |
| 3,763,507 A | * | 10/1973 | Propst ............................ | 5/100 |
| 3,786,523 A | * | 1/1974 | Sele ............................. | 5/87.1 |
| 3,902,204 A | * | 9/1975 | Lee ............................. | 5/86.1 |
| 3,962,736 A | * | 6/1976 | Fedele ..................... | 5/81.1 HS |
| 4,259,756 A | * | 4/1981 | Pace ....................... | 5/81.1 HS |
| 4,644,594 A | * | 2/1987 | Johnson .................... | 5/81.1 HS |
| 4,761,841 A | * | 8/1988 | Larsen ...................... | 5/81.1 C |
| 4,770,383 A | * | 9/1988 | Lehman et al. .......... | 248/188.1 |
| 4,873,732 A | * | 10/1989 | Perez ..................... | 5/81.1 HS |
| 5,005,230 A | * | 4/1991 | Congdon ...................... | 5/600 |
| 5,475,884 A | | 12/1995 | Kirmse et al. | |
| 5,493,741 A | * | 2/1996 | Baer ............................ | 5/86.1 |
| 5,619,763 A | * | 4/1997 | Randolph et al. ............. | 5/601 |
| 5,758,586 A | * | 6/1998 | Kieser et al. ............. | 108/147 |
| 6,484,332 B2 | * | 11/2002 | Korver et al. ............. | 5/81.1 R |

FOREIGN PATENT DOCUMENTS

| | | |
|---|---|---|
| DE | 30 34 932 | 4/1982 |
| DE | 90 15 210 | 3/1991 |
| DE | 43 19 524 | 12/1994 |

* cited by examiner

*Primary Examiner*—Teri Pham Luu
(74) *Attorney, Agent, or Firm*—Schiff Hardin LLP

(57) ABSTRACT

A patient support mechanism has a patient gurney for the delivery and removal of a patient, the patient gurney having a removable bed board, and having a stationary patient bed provided for the acceptance of the bed board or having a stationary supporting part provided therefor at an imaging medical system such as, for example, a CT installation, an angiography device or a NMR installation. The patient gurney has carriages that are transversely displaceable toward both sides for accepting the bed board and for shifting the bed board from the patient gurney onto the patient bed or onto the supporting part and vice versa. A patient gurney having two double T-shaped supports that are centrally connected to one another by a longitudinal support.

9 Claims, 2 Drawing Sheets

PATIENT GURNEY AND PATIENT SUPPORT MECHANISM

BACKGROUND OF THE INVENTION

1. Field of the Invention

The present invention is directed to a patient support mechanism with a patient gurney for the delivery and removal of a patient, of the type wherein the patient gurney has a removable bed board, and the support has a stationary patient bed provided for the acceptance of the bed board or a stationary supporting part provided therefor at an imaging medical system. The invention is also directed to a patient gurney.

2. Description of the Prior Art

In order to assure gentle interfacing with the patient, patient gurneys have been proposed that enable an x-ray examination of the patient without requiring a repositioning or transfer from the gurney onto some other bed, for instance onto a bed belonging to an x-ray apparatus, or onto a supporting part. For example, German OS 43 19 524 discloses a transport mechanism that has frames that are extensible drawer-like or telescope-like in the transverse direction, with which the patient lying on the bed can be laterally placed so that—undisturbed by metallic components—an x-ray image can be acquired by an x-ray detector inserted under the bed.

A similar moving mechanism is disclosed by German Utility Model 90 15 210. This has two bracket arms that are horizontally displaceable transversely to the longitudinal direction for placement onto an x-ray-transparent support mechanism.

The above-described patient support mechanisms, which are for repositioning or transfer of the patient, are known in a wide variety of embodiments for those instances wherein the patient must be transferred from the gurney—with or without a bed board—onto the patient bed or onto a supporting part of an imaging apparatus, the patient being able to be moved into the apparatus with the assistance thereof. Without such a repositioning or transfer, for example, the patient could not be introduced into the narrow opening of a computed or magnetic resonance tomography apparatus. The patient bed can in turn have a supporting part and a bed board.

A simplification achieved in the patient support mechanism proposed in German OS 30 34 932, wherein the bed board can be completely lifted off from the supporting part of the apparatus, so that it can be optionally employed as a bed board of the patient gurney. German OS 42 24 036 discloses that the bed board in such an arrangement be fashioned so as to be lifted completely off from a stationary patient bed and to be placed onto the patient bed. In both instances, this provides the possibility of moving the patient to an imaging apparatus on the bed board with the assistance of the patient gurney and to transfer the patient with the bed board onto the patient bed or the supporting part of the apparatus. In order to avoid the difficulty or needing several persons for transferring the patient, the patient gurney is fashioned U-shaped, i.e. it has U-shaped supports framing an opening toward one side, so that the gurney can be moved under the patient bed or the supporting part from the side.

This arrangement, however, has the disadvantage that the patient can only be transferred proceeding from one side, which is not possible at all in many instances due to constricted or other impeded spatial conditions, so that such a system cannot be utilized everywhere.

SUMMARY OF THE INVENTION

An object of the present invention is to provide a patient support mechanism of the type initially described which allows the patient gurney to be brought or coupled to the patient bed or the supporting part in a simple way proceeding from both sides. A further object is to provide a patient gurney which can be brought to or coupled to a bed or supporting part from both sides.

For achieving this object, carriages are inventively provided at the patient gurney for accepting the bed board and for shifting the bed board from the patient gurney onto the patient bed or onto the supporting part and vice versa, with the carriages being transversely displaceable toward both sides proceeding from a position of the bed board that is not transversely shifted.

The carriages can have brackets that are extensible in telescoping fashion.

As a result of the inventive, transversely displaceable carriage, it is no longer necessary that the entire gurney—as in the case of known U-shaped gurneys—move completely under the patient bed proceeding from the side in order to be able to shift the patient bed or the supporting part thereover. On the contrary, the gurney can be brought next to the patient support table at the left or right in a simple way, dependent on the given space conditions, in order to accomplish a shifting of the patient onto the bed board both from the left as well as from the right. The carriage or its telescopingly extensible brackets are displaceable toward the left as well as toward the right relative to the supporting frame of the gurney, in order to be able to accomplish shifting of the bed board with the assistance of only one attendant regardless of the side at which the gurney approaches the patient bed.

The inventive patient bearing mechanism has an especially simple form when the bed board is lengthened relative to the stationary patient bed or the stationary supporting part, so that two correspondingly spaced acceptance carriages at the patient gurney can have the projecting ends move under them. Due to the long length of the bed board that should generally not be significantly longer then the length of the stationary supporting part of the patient bed, problems arise with respect to the length of the patient gurney, so that the maneuverability thereof in the frequently narrow passages in hospitals is unsatisfactory.

In order to avoid these difficulties, the bed board can be mounted so as to be liftable at the patient bed or at the supporting part via at least one plunger or the like or, groove-shaped transverse recesses being provided in the supporting part into which the carriages or the telescopically extensible brackets of the carriages can be introduced in order to transfer a bed board onto the supporting part of the patient bed or remove it therefrom.

In an embodiment the patient gurney has supports that are preferably essentially I-shaped or double T-shaped, and preferably longitudinally strutted, whose upper transverse leg or transverse strut carries the carriages and whose lower transverse legs or transverse struts carry the running wheels. Such an I-shaped or double T-shaped gurney can be built far simpler and more torsionally stiff, because of the shorter load bearing length of the struts, than can the known U-shaped gurneys serving the purpose of being moved under a patient bed at one side.

The above object is also inventively achieved in a patient gurney that has supports connected to one another via a longitudinal carrier, preferably centrally, that each have an upper transverse strut and a lower transverse strut, the lower transverse struts carrying running wheels, and the upper transverse struts and the lower transverse struts projecting beyond the longitudinal carrier toward both sides—at least in a front view—, so that the supports are essentially I-shaped or double T-shaped.

In particular, the lower transverse struts are centrally connected to one another to form a travel frame, so that, for example, the ends of the transverse struts only carry the running wheels without having other connecting elements proceeding from these ends.

Preferably, the upper transverse struts have transversely displaceable carriages for accepting a bed board and for shifting the bed board onto a stationary supporting part and vice versa.

In particular, the carriages have brackets that can be extended in telescoping fashion. For example, the carriages have brackets seated inside one another that are essentially U-shaped and limited relative to one another in both directions.

DESCRIPTION OF THE PREFERRED EMBODIMENTS

Figure 1:
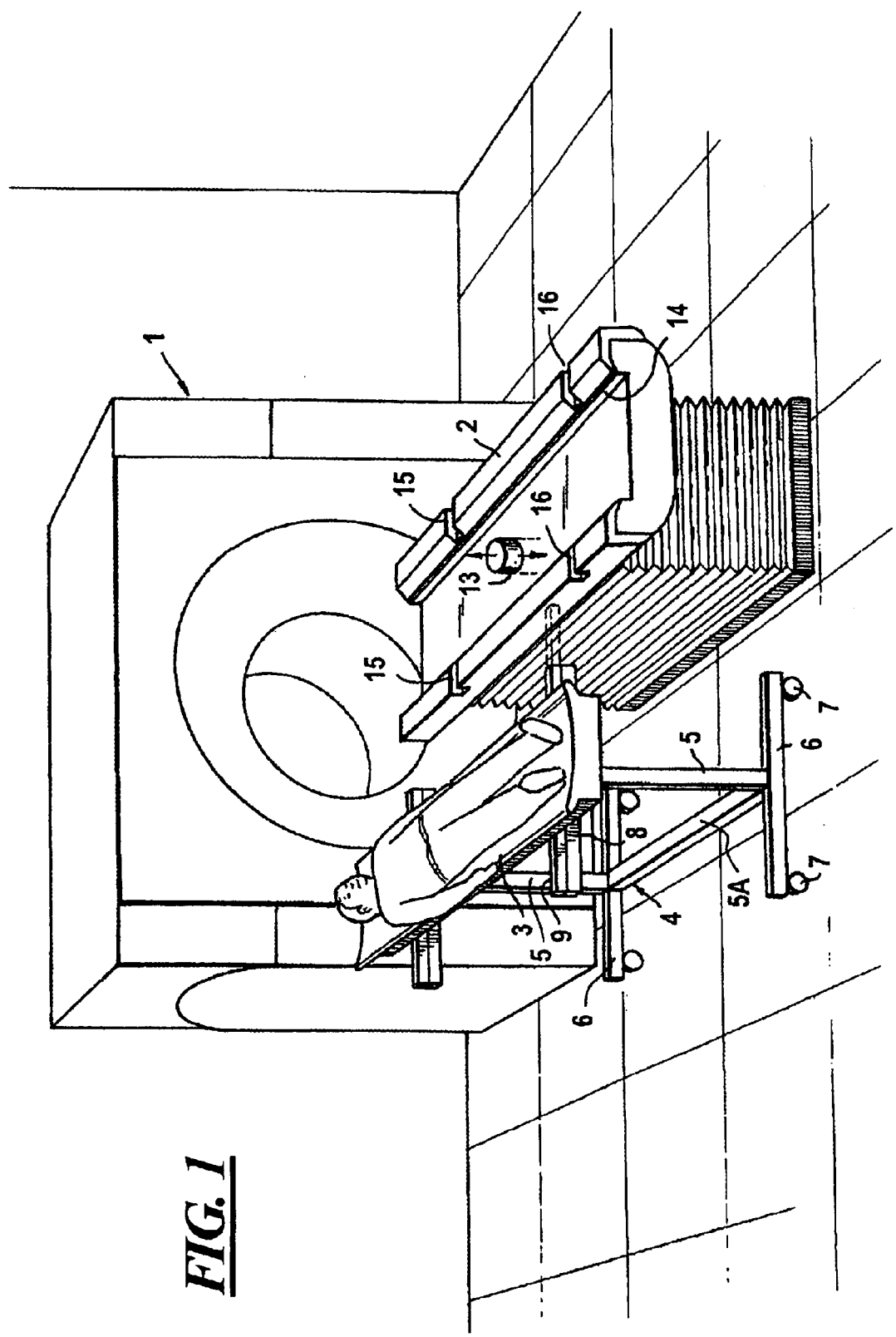
FIG. 1 is a perspective view of a CT system with patient bed and inventive patient gurney standing next to the patient bed.

FIG. 1 shows a patient support, such as a medical imaging system 1, a CT apparatus 1 in this case, having a stationary supporting part 2 or a patient bed on which a bed board 3 can be seated so as to be longitudinally displaceable, as shown on the gurney 4 standing next to it. The medical imaging system 1 alternatively can be a conventional x-ray apparatus, an angiography system, a NMR system or the like.

The gurney 4 has two essentially double T-shaped or I-shaped supports 5 having lower transverse struts 6 to which the running wheel 7 are secured and upper transverse struts 8 at which carriages 9 that are transversely displaceable in telescoping fashion are arranged, the bed board 3 being transferred with the assistance thereof from the stationary supporting part 2 of the patient bed onto the gurney or from the gurney 4 onto the stationary supporting part 2 of the patient bed. The two supports 5 are connected to one another in the lower region, specifically at the lower transverse struts 6 here, via a centrally secured and centrally proceeding longitudinal carrier 5A. The entire traveling frame of the gurney 4, formed by the two supports 5 and the longitudinally bracing longitudinal carrier 5A, is thus largely symmetrical relative to a vertical longitudinal plane that proceeds centrally through the gurney 4. The lower transverse struts 6 of the traveling frame project toward both sides with respect to the longitudinal carrier 5A, so that the traveling frame is open at both sides, and can travel around and under the stationary supporting part 2 up to half its width. In other words: the lower transverse beams, transverse supports or transverse struts 6 are cantilevered, i.e. they carry the running rollers 7 at their ends.

Figure 2:
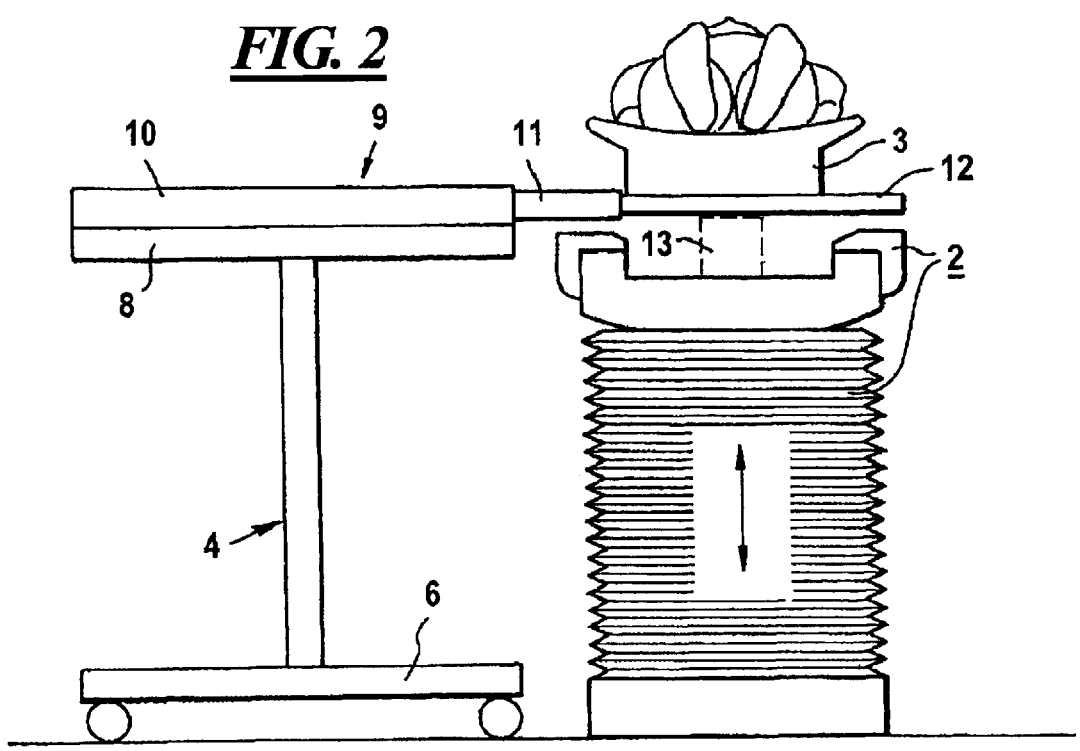
FIG. 2 is an end view of the patient support mechanism according to FIG. 1.
Figure 3:
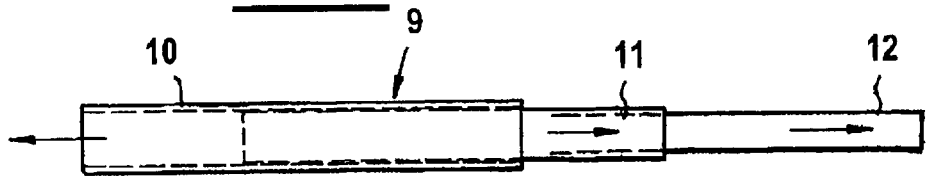
FIG. 3 is a plan view onto the transverse displacement carriage on one of the I-shaped supports of the patient gurney.
Figure 4:
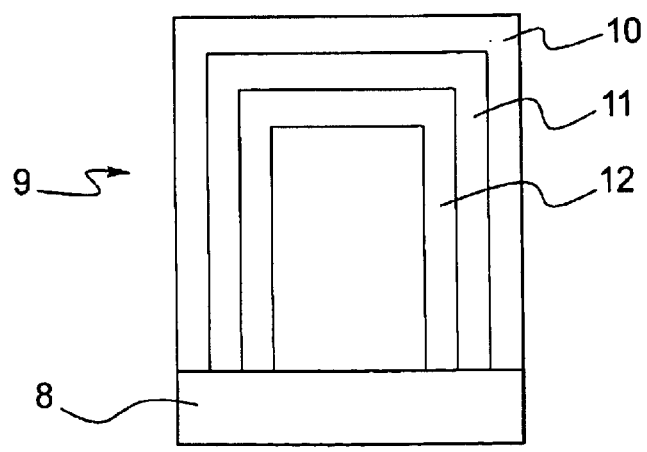
FIG. 4 is an end view showing U-rail-like brackets seated in an outer U-rail. corresponding to the plan view shown in FIG. 3.

In the simple exemplary embodiment shown in FIGS. 2 and 3 and 4, two U-rail-like brackets 11 and 12, that are limited to the left and right and that are displaceable in telescoping fashion, are seated in an outer U-rail 10 secured to the transverse strut 8, so that the bed board 3 lying on the somewhat raised edges of the U-rail 12 can be shifted from the patient gurney 4 toward the left or right and can be transferred onto the supporting part 2 of the patient bed. For this purpose a retractable and extensible plunger 13 can be arranged in the supporting part 2 of the patient bed in order to be able to optionally lift the bed board 3 and in turn lower it into the channel 14 of the supporting part 14. Alternatively, transverse channels 15 or 16 can be provided in the raised side parts of the supporting part 2 in order to retract and extend the telescoping arms 11, 12 of the displacement carriage 9 in order to be able to shift this without lifting the bed board.

The patient can be brought with the gurney 4 and—given the preferred adaptation of the patient beds or of the supporting parts of different imaging systems—can then be optionally transferred to the patient bed or the supporting part of the respectively required imaging system.

Although modifications and changes may be suggested by those skilled in the art, it is the intention of the inventor to embody within the patent warranted hereon all changes and modifications as reasonably and properly come with the scope of his contribution to the art.

I claim as my invention:

1. A patient support mechanism comprising:

a stationary patient support;

a patient gurney having a removable bed board adapted to be received at said stationary patient support upon removal from said patient gurney; and said patient gurney having carriages, each comprising telescopically extensible brackets, for accepting said bed board and for shifting said bed board from said patient gurney onto said patient support, said bed board occupying an unshifted position on said patient gurney and said carriages being transversely displaceable on opposite sides of said unshifted position allowing shifting of said bed board relative to said gurney at both of said sides.

2. A patient support mechanism as claimed in claim 1 wherein said stationary patient support is a patient bed.

3. A patient support mechanism as claimed in claim 1 wherein said stationary patient support is a patient supporting part of a medical imaging system.

4. A patient support mechanism as claimed in claim 1 wherein each of said carriages comprises a first bracket having a U-shaped cross section and a second bracket having a U-shaped cross section, said first bracket being displaceably seated inside said second bracket so that said first and second brackets are displaceable relative to each other in two directions respectively towards said sides.

5. A patient support mechanism as claimed in claim 1 wherein said bed board has a longitudinal length which is longer than a longitudinal length of said stationary patient support.

6. A patient support mechanism as claimed in claim 1 wherein said patient support comprises a lifting element on which said bed board is disposed when said bed board is on said patient support, said lifting element being operable to lift said bed board vertically off of said patient support.

7. A patient support mechanism as claimed in claim 1 wherein said patient gurney comprising two double T-shaped supports each having an upper transverse strut and a lower transverse strut, and said patient gurney having at least one longitudinal strut connecting said double T-shaped supports, and that running wheels respectively mounted on said lower transverse struts, said upper transverse struts carrying said carriages.

8. A patient gurney comprising:

first and second supports spaced from each other and connected to each other by a longitudinal carrier, each of said supports having an upper transverse strut and a lower transverse strut;

running wheels melted on each of said lower transverse struts, each of said upper transverse struts and said lower transverse struts projecting beyond said longitudinal carrier at opposite sides of said longitudinal carrier so that each of said supports is substantially double T-shaped, wherein each of said upper transverse struts comprise transversely displaceable carriages, and wherein said gumey further comprises a bed board accepted on said carriages, said carriages being operable to shift said bed board selectively toward either of said sides.

9. A patient gurney as claimed in claim 8 wherein each of said carriages comprises telescopically extensible brackets.

\* \* \* \* \*